United States Patent [19]
Simmons

[11] Patent Number: 5,925,052
[45] Date of Patent: Jul. 20, 1999

[54] UMBILICAL SURGICAL SCISSORS

[76] Inventor: Paul L. Simmons, 8825 Laurel Dr., Pinellas Park, Fla. 33782

[21] Appl. No.: 08/882,180

[22] Filed: Jun. 25, 1997

Related U.S. Application Data

[60] Provisional application No. 60/020,626, Jun. 26, 1996.

[51] Int. Cl.$^6$ .............................................. A61B 17/1412
[52] U.S. Cl. ........................ 606/120; 606/108; 606/139
[58] Field of Search .................................. 606/120, 108, 606/205, 210, 139

[56] References Cited

U.S. PATENT DOCUMENTS

| | | | |
|---|---|---|---|
| 352,245 | 11/1886 | Hullhorst | 606/120 |
| 3,166,071 | 1/1965 | Mayer | 606/120 |
| 4,428,374 | 1/1984 | Auburn | 606/120 |
| 5,591,173 | 1/1997 | Schifano | 606/120 |

*Primary Examiner*—Michael Buiz
*Assistant Examiner*—(Jackie)Tan-Uyen Thi Ho
*Attorney, Agent, or Firm*—A. W. Fisher, III

[57] ABSTRACT

Umbilical surgical scissors to cut and clamp the umbilical cord following birth comprising a scissor assembly including a first and second scissor member selectively movable between a first and second position relative to each other having a clamping assembly detachably mounted thereon by a clamp assembly holder, the clamping assembly comprises a pair of clamping clips each including a first and second clamping element movable between a normally open position and a closed clamping position such that when the first and second scissor members are moved from the first position to the second position the umbilical cord is severed and the responding first and second clamping elements clamp the umbilical cord therebetween.

9 Claims, 2 Drawing Sheets

1

UMBILICAL SURGICAL SCISSORS

CROSS REFERENCE

This is a regular patent application claiming priority and converted from the provisional patent application filed Jun. 26, 1996 assigned application Ser. No. 60/020,626.

BACKGROUND OF THE INVENTION

1. Field of the Invention

Umbilical surgical scissors to cut and clamp off the umbilical cord following birth.

2. Description of the Prior Art

In the medical field there are currently many instruments, both permanent and reusable, and disposable, that perform the cutting function. There also exists clamps, both permanent and reusable, and disposable in the medical field, for clamping onto structures to hold, stop the flow of, or perform any such clamping function. In particular, during the birth process, it becomes necessary to separate the newborn from the umbilical cord to which it is attached. This is currently done by clamping of two sections of the cord in close proximity to each other and then cutting it. Any blood and/or body fluids contained within the cord between the two clamps will fall, drip, splatter out away from the cut and could adhere to medical personnel in the adjacent area.

In addition to individual simple cutting and clamping devices, there exists clamping and cutting devices for simultaneously clamping and cutting a material comprising two separable clamping devices assembled in side-by-side abutting relation with the abutting sides of the clamping devices being provided with cooperating releasable means holding them in abutting relation. There exists cutting shears having a gripping device for holding an item to be cut including cooperating jaw members mounted on the cutting blades.

U.S. Pat. No. 3,323,208 describes a clamping and cutting means for simultaneously clamping and cutting a material comprising two separable clamping devices assembled in side-by-side abutting relation with the abutting sides of the clamping devices being provided with cooperating releasable means holding them in abutting relation. Each clamping device comprises a pair of elongated clamping elements having a hinged connection at one end with the elements with cooperating clamping faces and latch means at the other end for holding the elements in clamping relation. Cooperating finger-piece means on the clamping devices extend the full width of the side-by-side clamping devices on the exterior thereof whereby pressure applied thereto will simultaneously move the two clamping devices into clamping relation. A knife means formed on one of the clamping devices projects above the clamping face of the element and into cooperative relation with a slot formed in the other clamping element whereby material disposed between the elements of the clamping device will be severed incident to the clamping thereof.

U.S. Pat. No. 3,520,058 shows a cutting shear having a gripping device for holding an item to be cut including cooperating jaw members mounted on the cutting blades. One jaw member is fixed to one blade and the other jaw member is slidably and pivotally supported relative to the other blade and biased by a spring toward the one jaw member and against the one jaw member when the shear is closed. The jaw members being aligned with or coplanar of the cutting edges on the blades when the shear is opened fully.

U.S. Pat. No. 5,203,084 teaches a pair of scissors with pincher-clip to control the opening angle when opened and the locking of the scissors when closed. The scissors with pincher-clip can achieve its function by moving on one side. The limitation of its opening is achieved by a 0-shaped buckle that connects to the spring coils on one side and a long groove of the handle on the other side. Following the opening of the pair of scissors, the 0-shape buckle moves up and down in the long groove, thus controlling the opening angle of the pair of scissors by the distance between the spring coils and the pivot and locking the pair of scissors when it is closed.

U.S. Pat. No. 5,170,559 describes a cutting blade of rose-gripping shears cooperating with an angle comprising an clamping plate resting against the anvil in the closed position movable together with the cutting blade. The clamping piece can move backwards under spring action in order to hold a cut stem between the clamping plate and the anvil. The spring urging of the clamping piece is obtained by a spring arm which extends in an arcuate section around the swivel pin between the shear arms and comes against a mounting plate which is connected, fixed for rotation, to the gripping lever of the cutting blade.

U.S. Pat. No. 4,092,774 shows a cutting device for cutting tubing including a first and second elongated handle member pivotally secured together at one end so that the handle members are movable relative to each other between an open and closed position. Semicircular and facing recesses are formed along the inner side of the handle members which correspond in shape to the outer periphery of the plastic tubing which is to be cut. With the plastic tubing between the handle members, the handle members are closed clamping the tubing between the semi-circular recesses. A cutting blade is pivotally secured to one of the handle members so that the cutting blade can be moved across the handle members to cut the tubing.

U.S. Pat. No. 5,095,622 teaches an apparatus comprising an upper jaw including a concave recess cooperating with a coaxially aligned planar surface wherein a bottom jaw provides a cooperating planar clamping surface to cooperate with the upper clamping surface and to effect a severing of a suture and the like secured between the upper and lower jaws.

U.S. Pat. No. 4,744,145 describes a hair parting and grasping cutter for parting, grasping, lifting and cutting a person's hair conveniently by one hand operation comprising a frame, an upper shear, an upper shear casing and a lower shear. The elongated upper and lower portions of the frame each comprises in sequence of a front portion, an arm portion with a slot, a handle portion and a spring portion which is joined to a rear end of the frame, so as to be closed each other to grasp the hair by the squeezing strength of a user's hand onto the handle portions. The sharp ended front portions are inserted to the hair to part the desired section of the hair. The upper shear casing is fixedly attached to the upper arm portion within the upper slot and the upper shear is pivotably attached to near the front end of the upper shear casing. A spring strip to force the upper shear upwardly and an upperwall to stop the upper shear are one-piece body with the upper shear casing. The lower shear is fixedly attached to the lower arm portion within the lower slot. An actuator pivotably attached to the rear of the upper shear has a spring strip projected from an upperwall of the actuator to force the rear end of the actuator downwardly. By pressing the top of the actuator with a tip of a finger of the same hand, the blade cutting edges of the shears are contacted and overlapped each other to cut the hair.

U.S. Pat. No. 3,783,875 shows a surgical tool fashioned from scissors having an attached cam member for moving along the lateral face of one scissor member thereby crushing skin position between the cam and lateral face which seals veins and arteries along the crushed line. Scissor action follows the crushing action and severs skin along the crushed line instantaneously.

SUMMARY OF THE INVENTION

The present invention relates to umbilical surgical scissors comprising a scissor assembly having a clamping assembly detachably mounted thereon by a clamp assembly holder to cut and clamp off the umbilical cord following birth.

The scissor assembly comprises a first and second scissor member and selectively movable between a first or open position and a second or closed position. The first scissor member comprises a first handle having a blade element formed on one end portion thereof; while, the second scissor member comprises a second handle having a clamping assembly holder support formed on one end portion thereof. The blade element comprises a blade member having a cutting edge and a clamping assembly limit or stop including a clip post or pin extending outwardly from each side of the blade member to engage a portion of the clamping assembly. The clamping assembly holder support comprises a pair of support members to support the clamp assembly holder.

The clamp assembly holder comprises a pair of clamp supports disposed on opposite sides of a cutting surface disposed in the same plane as the blade member to operatively engage the cutting edge when the first and second scissor members are moved from the first or open position to the second or closed position and a retainer channel to receive the support members therein to retain the clamp assembly holder on the clamping assembly holder support.

Each clamp support comprises an arcuate or concave clip retainer member to receive and secure the clamping assembly to the clamp assembly holder as described more fully hereinafter.

The clamping assembly includes a pair of clamping clips each comprising a first and second elongated clamping element hingedly attached at one end portion thereof by an arcuate or convex hinge member and a first and second locking element formed on the opposite end portions of the first and second elongated clamping elements respectively.

To assemble, the clamping clips are mounted on the clamp assembly holder by placing the arcuate or convex hinged member into the corresponding arcuate or concave clip retainer. So assembled, the clamp assembly holder is secured to the scissors assembly by placing the retainer channel over the clamping assembly holder support. Each clip stop or pin engages the first elongated clamping element of the corresponding clamping clip to control the closing and locking thereof.

In use, the umbilical surgical scissors are operably placed relative to the umbilical cord. Then the first and second scissor members are moved from the first position to the second position such that the cutting edge cuts the umbilical cord as the corresponding first and second lock elements engage each other to lock the corresponding first and second elongated clamping elements together to clamp the umbilical cord therebetween.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
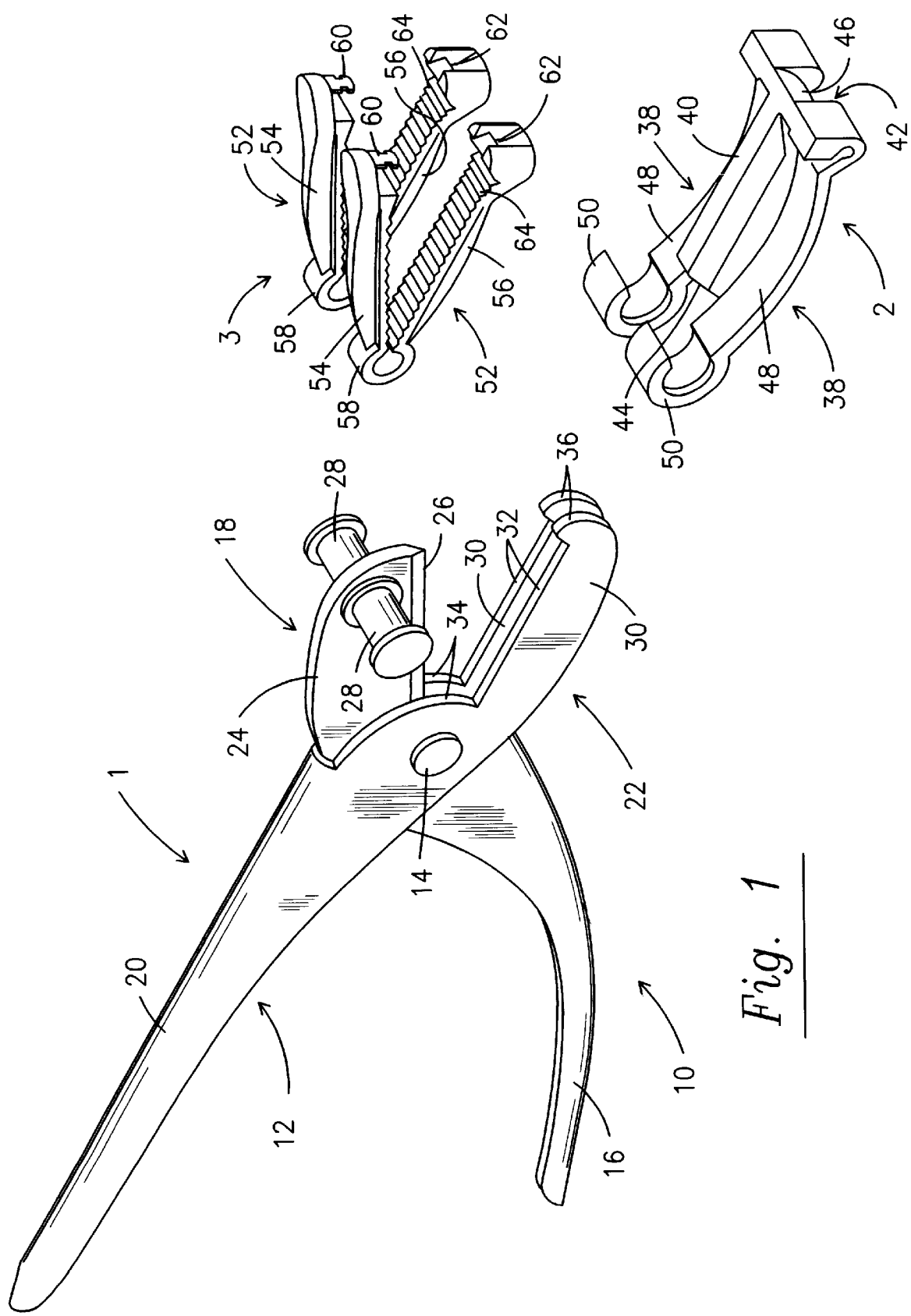
FIG. 1 is a perspective exploded view of the umbilical surgical scissors of the present invention.
Figure 2:
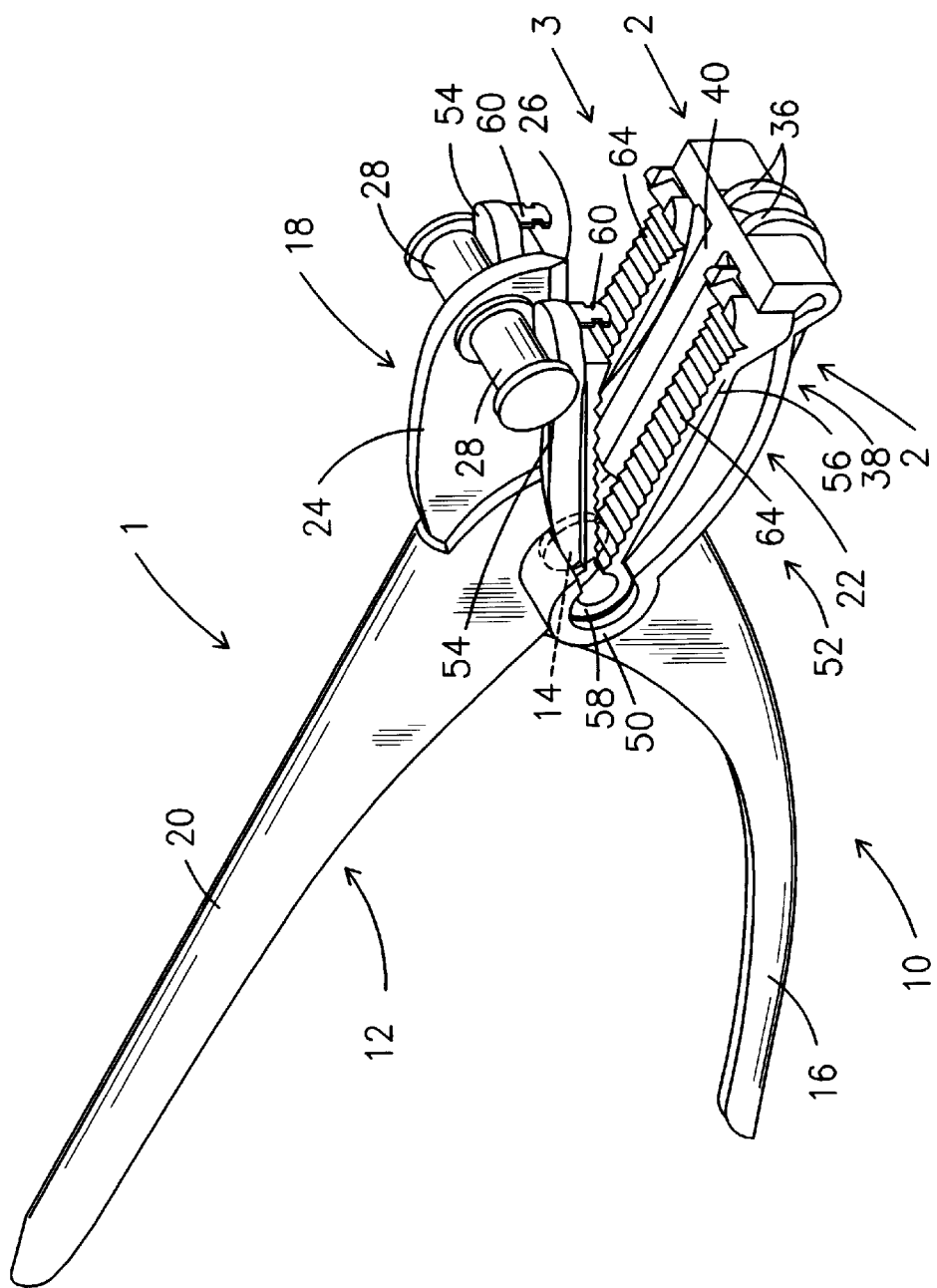
FIG. 2 is a perspective view of the umbilical surgical scissors of the present invention.

AS shown in FIGS. 1 and 2, the present invention relates to umbilical surgical scissors comprising a scissor assembly 1 having a clamping assembly 3 detachably mounted thereon by a clamp assembly holder 2 to cut and clamp off the umbilical cord following birth.

The scissor assembly 1 comprises a first and second scissor member 10 and 12 respectively pivotally coupled together by a pivot member 14 and selectively movable between a first or open position (as shown) and a second or closed position (not shown). The first scissor member 10 comprises a first handle 16 having a blade element 18 formed on one end portion thereof; while, the second scissor member 12 comprises a second handle 20 having a clamping assembly holder support 22 formed on one end portion thereof adjacent the blade element 18. The blade element 18 comprises a blade member 24 having a cutting edge 26 formed on the lower surface thereof and a clamping assembly limit or stop including a clip post or pin 28 extending outwardly from each side of the blade member 24 to engage a portion of the clamping assembly 3 as described more fully hereinafter. The clamping assembly holder support 22 comprises a pair of support members each indicated as 30 having a clamp holder support surface 32 to support the clamp assembly holder 2 thereon and an inner and outer clamp holder retainer member indicated as 34 and 36 respectively to retain the clamp assembly holder 2 therebetween.

The clamp assembly holder 2 comprises a pair of clamp supports each 38 disposed on opposite sides of a cutting surface 40 disposed in the same plane as the blade member 24 to operatively engage the cutting edge 26 when the first and second scissor members 10 and 12 are moved from the first or open position to the second or closed position and a retainer channel 42 having an inner and outer retainer surface indicated as 44 and 46 respectively at opposite ends thereof to receive the support members 30 therein and to engage the inner and outer clamp holder retainer members 34 and 36 respectively to retain the clamp assembly holder 2 on the clamping assembly holder support 22.

Each clamp support 38 comprises a clip support surface 48 and an arcuate or concave clip retainer member 50 to receive and secure the clamping assembly 3 to the clamp assembly holder 3 as described more fully hereinafter.

The clamping assembly 3 comprises a pair of commercially available clamping clips each indicated as 52 similar to those described in U.S. Pat. No. 4,092,774. Each clamping clip 52 comprises a first and second elongated clamping element indicated as 54 and 56 respectively hingedly attached at one end portion thereof by an arcuate or convex hinge member 58 and a first and second locking element indicated as 60 and 62 respectively formed on the opposite end portion of the first and second elongated clamping elements 54 and 56 respectively. The first and second locking elements 60 and 62 comprise a cooperating latch and abutment means, tongue and slot or other corresponding elements suitably configured to mate and securely lock with each other when engaged. The first and second elongated clamping elements 54 and 56 may further include a plurality of mating teeth indicated as 64 to enhance the gripping action of the umbilical cord.

To assemble, a clamping clip 52 is mounted to each of the clamp supports 38 by placing the arcuate or convex hinged member 58 into the corresponding arcuate or concave clip retainer member 50 with the second elongated clamping element 56 disposed on the corresponding clip support surface 48. So assembled, the clamp assembly holder 2 is secured to the scissors assembly 1 by placing the retainer channel 42 over the clamping assembly holder support 22 and press-fitting the inner and outer retainer surfaces 44 and 46 of the clamp assembly holder 2 between the inner and outer clamp holder retainer members 34 and 36. AS best shown in FIG. 2, each clip post or pin 28 engages the first elongated clamping element 56 of the corresponding clamping Clip 52 to control the closing and locking thereof.

In use, the umbilical surgical scissors are operably placed relative to the umbilical cord. Then the first and second scissor members 10 and 12 are moved from the first position to the second position such that the cutting edge 26 engages the cutting surface 40 to cut the umbilical cord as the corresponding first and second lock elements 60 and 62 engage each other to lock the corresponding first and second elongated clamping elements 54 and 56 together to clamp the umbilical cord therebetween.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. Umbilical surgical scissors to cut and clamp the umbilical cord following birth comprising a scissor assembly having a clamping assembly detachably mounted thereon by a clamp assembly holder, said scissor assembly includes a first and second scissor member pivotally coupled together and selectively movable between a first and second position relative to each other, said first scissor member includes a cutting element formed on one end portion thereof and said second scissor member includes a clamping assembly holder support formed on one end portion thereof configured to operatively support a portion of said clamping assembly holder thereon, said clamping assembly comprises a pair of clamping clips each including a first and second clamping element hingedly coupled to each other on one end portion thereof and movable between a normally open position and a closed clamping position relative to each other and a corresponding first and second lock element formed on the opposite end portions of said first and second clamping elements repectively wherein said clamping assembly holder support comprises a pair of support members each having a clamp holder support surface to support said clamp assembly holder thereon and an inner and outer clamp holder retainer member to retain said clamp assembly holder therebetween and said clamp assembly holder comprises a pair of clamp supports disposed on opposite sides of a cutting surface disposed in the same plane as said cutting element to operatively engage said cutting element when said first and second scissor members are moved from said first positions to said second positions and having an inner and outer retainer surface at opposite ends thereof to engage said inner and outer clamp holder retainer members respectively to press-fit said clamp assembly holder therebetween to retain said clamp assembly holder on said clamping assembly holder support such that when said first and second scissor members are moved from said first position to said second position said cutting element cuts the umbilical cord as said first and second lock elements engage each other to lock said first and second clamping elements together to clamp the umbilical cord therebetween, each said corresponding first and second clamping elements is hingedly attached by a convex hinge member and each said clamp support includes a corresponding concave clip retainer member to receive said corresponding convex hinge member therein to secure each said clamping clip to said clamp assembly holder, said cutting element further includes a clip post extending outwardly from each side thereof to slidingly engage one of said first elongated clamping elements to control the movement thereof between said corresponding first positions to said corresponding second positions.

2. The umbilical surgical scissors of claim 1 wherein said corresponding first and second clamping elements further include a first and second locking element respectively formed on the opposite end portions from said corresponding convex hinge member of said first and second clamping elements.

3. The umbilical surgical scissors of claim 2 wherein said corresponding first and second clamping elements each further includes a plurality of mating teeth to enhance the gripping action of said clamp assembly on the umbilical cord.

4. The umbilical surgical scissors of claim 1 wherein said first scissor member comprises a first handle having a blade element formed on one end portion thereof and said second scissor member comprises a second handle having said clamping assembly holder support formed on one end portion thereof adjacent said blade element.

5. The umbilical surgical scissors of claim 1 wherein said clamp assembly holder further includes a retainer channel to receive said support members therein to secure said clamp assembly holder laterally on said clamping assembly holder support when said umbilical surgical scissors are operatively assembled.

6. Umbilical surgical scissors to cut and clamp the umbilical cord following birth comprising a scissor assembly having a clamping assembly detachably mounted thereon by a clamp assembly holder, said scissor assembly includes a first and second scissor member pivotally coupled together and selectively movable between a first and second position relative to each other, said first scissor member includes a cutting element formed on one end portion thereof and said second scissor member includes a clamping assembly holder support formed on one end portion thereof configured to operatively support a portion of said clamping assembly holder thereon, said clamping assembly comprises a pair of clamping clips each including a first and second clamping element hingedly coupled to each other on one end portion thereof and movable between a normally open position and a closed clamping position relative to each other and a corresponding first and second lock element formed on the opposite end portions of said first and second clamping elements respectively wherein said clamping assembly holder support comprises a pair of support members each having a clamp holder support surface to support said clamp assembly holder thereon and an inner and outer clamp holder retainer member to retain said clamp assembly holder therebetween and said clamp assembly holder comprises a pair of clamp supports disposed on opposite sides of a cutting surface disposed in the same plane as said cutting element to operatively engage said cutting element when said first and second scissor members are moved from said first positions to said second positions and having an inner and outer retainer surface at opposite ends thereof to engage said inner and outer clamp holder retainer members respectively to press-fit said clamp assembly holder therebetween to retain said clamp assembly holder on said clamping assembly holder support such that when said first and second scissor members are moved from said first position to said second position said cutting element cuts the umbilical cord as said first and second lock elements engage each other to lock said first and second clamping elements together to clamp the umbilical cord therebetween, each said corresponding first and second clamping elements is hingedly attached by a convex hinge member and each said clamp support includes a corresponding concave clip retainer member to receive said corresponding convex hinge member therein to secure each said clamping clip to said clamp assembly holder, said clamp assembly holder further includes a retainer channel to receive said support members therein to secure said clamp assembly holder laterally on said clamping assembly holder support when said umbilical surgical scissors are operatively assembled and said cutting element including a clip post extending outwardly from each side thereof to slidingly engage one of said first elongated clamping elements to control the movement thereof between said corresponding first positions to said corresponding second positions.

7. The umbilical surgical scissors of claim 6 wherein said corresponding first and second clamping elements further include a first and second locking element respectively formed on the opposite end portions from said corresponding convex hinge member of said first and second clamping elements.

8. The umbilical surgical scissors of claim 7 wherein said corresponding first and second clamping elements each further includes a plurality of mating teeth to enhance the gripping action of said clamp assembly on the umbilical cord.

9. The umbilical surgical scissor of claim 6 wherein said first scissor member comprises a first handle having a blade element formed on one end portion thereof and said second scissor member comprises a second handle having said clamping assembly holder support formed on one end portion thereof adjacent said blade element.

\* \* \* \* \*